United States Patent [19]
Hoshino et al.

[11] Patent Number: 5,428,175
[45] Date of Patent: Jun. 27, 1995

[54] PHYSIOLOGICALLY ACTIVE COMPOUND

[75] Inventors: Tsutomu Hoshino; Takeo Uchiyama, both of Niigata; Kenichi Kimura, Utsunomiya; Hidetoshi Takahashi, Minami-Kawachimachi; Makoto Yoshihama, Utsunomiya, all of Japan

[73] Assignee: Snow Brand Milk Products Co., Ltd., Hokkaido, Japan

[21] Appl. No.: 198,463

[22] Filed: Feb. 18, 1994

[30] Foreign Application Priority Data

Feb. 22, 1993 [JP] Japan .................................. 5-056510

[51] Int. Cl.$^6$ ............................................ C07D 403/14
[52] U.S. Cl. ................................................ 548/455
[58] Field of Search ....................................... 548/455

[56] References Cited

U.S. PATENT DOCUMENTS

| | | |
|---|---|---|
| 3,509,165 | 4/1970 | Ellzey et al. . |
| 4,529,698 | 7/1985 | Sykes et al. . |
| 4,595,698 | 6/1986 | Umezawa et al. .................. 514/456 |
| 4,737,461 | 4/1988 | Sugisawa et al. . |
| 4,752,469 | 6/1988 | Sykes et al. . |
| 4,859,593 | 8/1989 | Umezawa et al. . |
| 4,977,138 | 12/1990 | Okuhara et al. ...................... 514/10 |
| 4,985,365 | 1/1991 | Mitsuda et al. . |

FOREIGN PATENT DOCUMENTS

| | | |
|---|---|---|
| 0133550 | 2/1985 | European Pat. Off. . |
| 0304157 | 2/1989 | European Pat. Off. . |
| WO91/04975 | 4/1991 | WIPO . |

OTHER PUBLICATIONS

Tsutomu Hoshino et al., "Biosynthesis of Violacein: Evidence for the Intermediacy of 5-Hydroxy-L-tryptophan and the structure of a New Pigment, Oxyviolacein, Produced by the Metabolism of 5-Hydroxytryptophan", *Agric. Biol. Chem.*, 54(9):2339-2346 (1990).

Patrick J. Davis, et al., "Metabolism of N-Carbobenzoxyl-L-Tryptophan By Chromobacterium Violaceum", *Biochimica et Biophysica Acta*, 385(1):133-144 (1975).

Carol H. Letendre, et al., "The Tryptophan Hydroxylase of Chromobacterium Violaceum", *The J. of Biological Chemistry*, 249(22):7186-7191 (1974).

Tsutomu Hoshino et al., "A New Metabolite of Tryptophan, Chromopyrrolic Acid, Produced by Chromobacterium Violaceum", *Bioscience, Biotechnology, And Biochemistry*, 57(5):775-781 (1993).

Tsutomu Hoshino et al., "Formations of (5-Hydroxy)indole S-(−)-lactic Acid, N-Acetyl-5-hydroxy-L-tryptophan and (5-Hydroxy)indole Carboxylic Acid in the Metabolism of Tryptophan and 5-Hydroxy-tryptophan by Chromobacterium Violaceum", *Bioscience, Biotechnology, and Biochemistry*, 57(9):1609–1610 (1993).

Tsutomu Hoshino et al., "Biosynthesis of Violacein: a Novel Rearrangement in Tryptophan Metabolism With a 1,2-Shift of the Indole Ring", *Agric. Biol. Chem.*, 51(3):965–968 (1987).

Patrick J. Davis et al., "Formation of Indole-3-Carboxylic Acid by Chromobacterium Violaceum", *J. of Bacteriology*, 544–546 (Apr. 1976).

P. J. Davis et al., "Formation of Indole-3-Carboxylic Acid From Tryptophan by Chromobactyerium Violaceum", *J. of Natural Products*, 38(6):541 (Nov.–Dec. 1975).

*Primary Examiner*—David B. Springer
*Attorney, Agent, or Firm*—Testa, Hurwitz & Thibeault

[57] ABSTRACT

A physiologically active compound HS-1 having the following chemical structure is disclosed. This compound is prepared by culturing Chromobacterium violaceum, adding tryptophan and diethyldithiocarbamate (diethyldithiocarbamic acid) to the culture broth for reacting with the cells for producing HS-1 in the cells, and collecting the compound from the culture broth. This novel compound possesses antitumor and antimicrobial activity, and is effective as an antitumor agent or an antimicrobial agent.

(Abstract continued on next page.)

continued
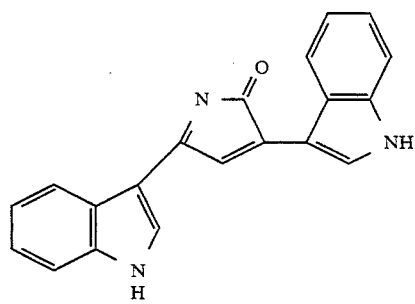
1 Claim, 4 Drawing Sheets

PHYSIOLOGICALLY ACTIVE COMPOUND

BACKGROUND OF THE INVENTION

1. Field of the Invention

The present invention relates to a physiologically active compound HS-1 of the following formula (I) and to a process for preparing the same. The physiologically active compound HS-1 is useful as an antitumor agent or an antimicrobial agent.

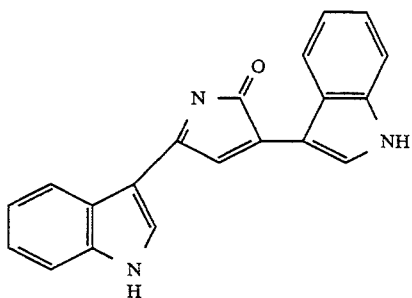

(I)

2. Description of the Background Art

Chromobacterium violaceum is known as a microorganism producing a purple pigment. This purple pigment is named violacein (Beer, R. J., et al., J. Chem. Soc., 885 (1949); (Beer, R. J., et al., J. Chem. Soc., 755 (1958)) and known to exhibit antimicrobial and antiprotozoal activities. This microorganism which produces violacein is known also to produce some physiologically active compounds other than violacein (HOSHINO, T. et al., Agric. Biol Chem., 54(9), 2339 (1990)).

Antitumor agents which are currently on actual use do not exhibit their activity on carcinoma based on distinct differences between cancer cells and normal cells, but identify cancer cells based on their vigorous division and growth activities, the capability of attracting substances, or the insufficient metabolizing activity. Selective toxicity actions of the conventional antitumor agents are therefore reduced on cancer cells which grow slowly. Because of this reason, most antitumor agents currently on use accompany serious side effects such as toxicity to heart, alopecia, gingivostomatitis, leukopenia, and gastrointestinal injury. The conventional antitumor agents have also a problem of drug tolerance. Therefore, there has been a desire for the development of a compound which can exhibit an antitumor activity based on a mechanism different from those in conventional antitumor agents.

The present inventors have undertaken screening of various compounds produced by Chromobacterium violaceum which is the violacein-producing microorganism, and, among compounds produced by Chromobacterium violaceum in the presence of tryptophan, discovered a novel compound HS-1, having the chemical structure represented by the formula (I) below and exhibiting toxicity against cancer cells.

SUMMARY OF THE INVENTION

Accordingly, an object of the present invention is to provide a novel physiologically active compound HS-1 represented by the following chemical formula (I),

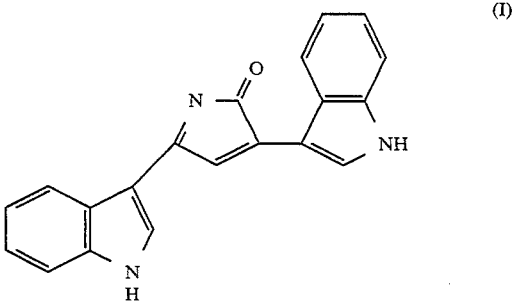

(I)

or a pharmaceutically acceptable salt thereof.

Another object of the present invention is to provide a process of preparing this novel physiologically active compound HS-1, which comprises:

culturing Chromobacterium violaceum capable of producing a physiologically active compound HS-1, adding tryptophan and diethyldithiocarbamate (diethyldithiocarbamic acid) to the culture broth for reacting with microorganism cells grown in the culture broth, and collecting the physiologically active compound HS-1 from the culture broth.

Other and further objects, features and advantages of the present invention will appear more fully from the following description.

BRIEF DESCRIPTION OF THE INVENTION

DETAILED DESCRIPTION OF THE INVENTION AND PREFERRED EMBODIMENTS

Violacein has the chemical structure of the following formula.

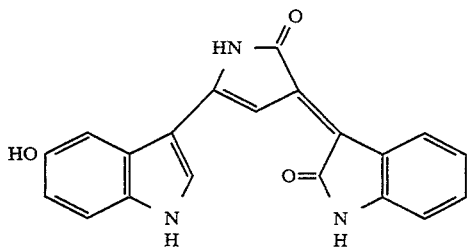

Directing an attention to the violacein, the present inventors have undertaken studies concerning the metabolism which various compounds undergo when added to a medium in which Chromobacterium violaceum is cultured and discovered a novel physiologically active compound HS-1 in the culture broth and the cells.

This physiologically active compound is considered to be produced in the course of biosynthesis of violacein. This compound have an indole structure which is possessed by none of antitumor compounds known in the art. A number of advantages and specific activities, such as in vivo absorption, excretion, stability, and reduced side effects, which have not been possessed by known compounds, are expected in this novel compound.

Physicochemical characteristics of the physiologically active compound HS-1 are as follows.

<Physicochemical Characteristics>

Figure 1:
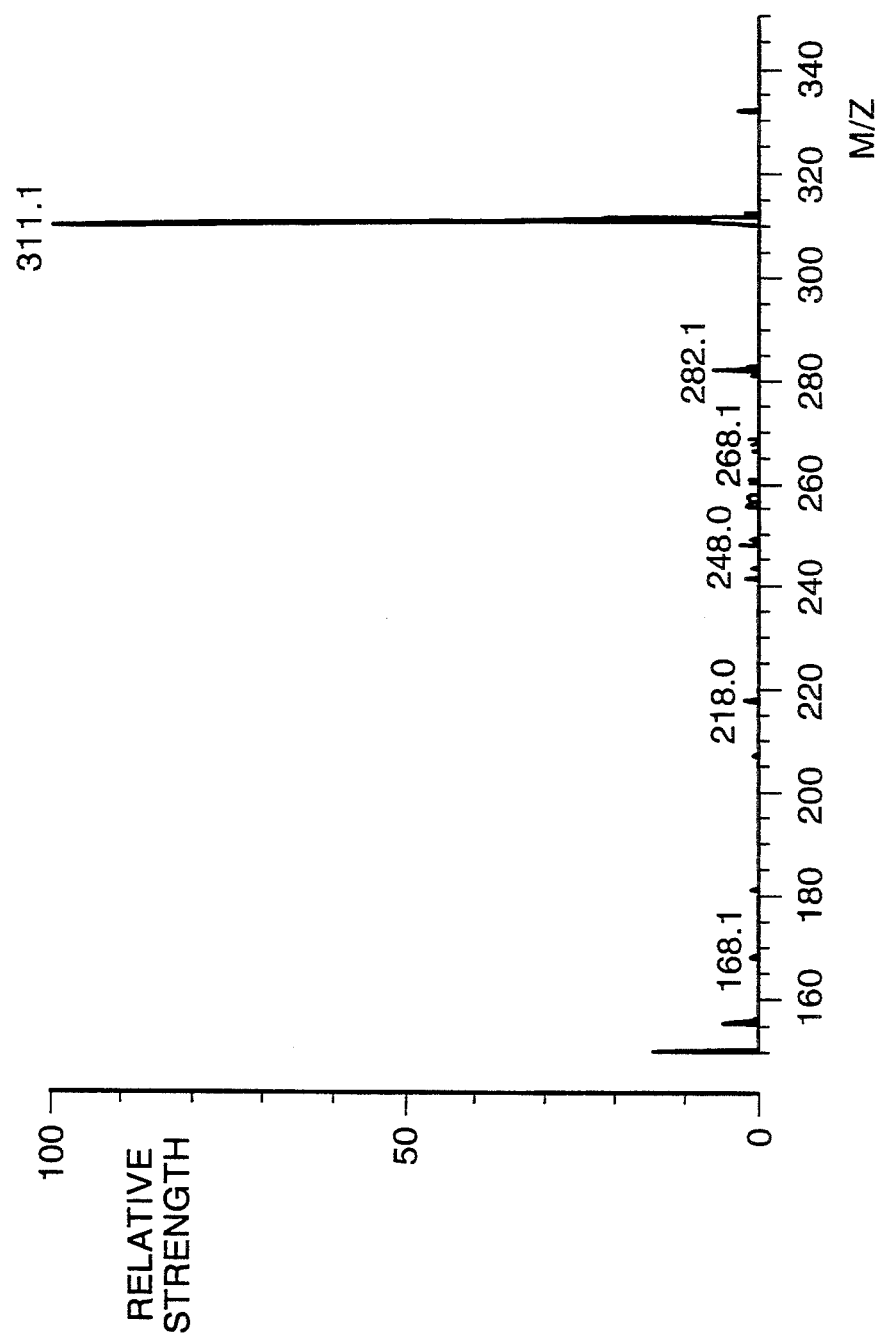
FIG. 1 is an electron ionization mass spectrometry (EI-MS) chart of the physiologically active compound HS-1.

(1) Molecular formula
$C_{20}H_{13}N_3O$ (2) Mass spectrum (EI-MS)
(M)+ = 311 (See FIG. 1)

(3) High resolution mass spectrum (HREI-MS)
Theoretical: 311.10586
Found: 311.10426

(4) Melting point
Above 275° C.

Figure 2:
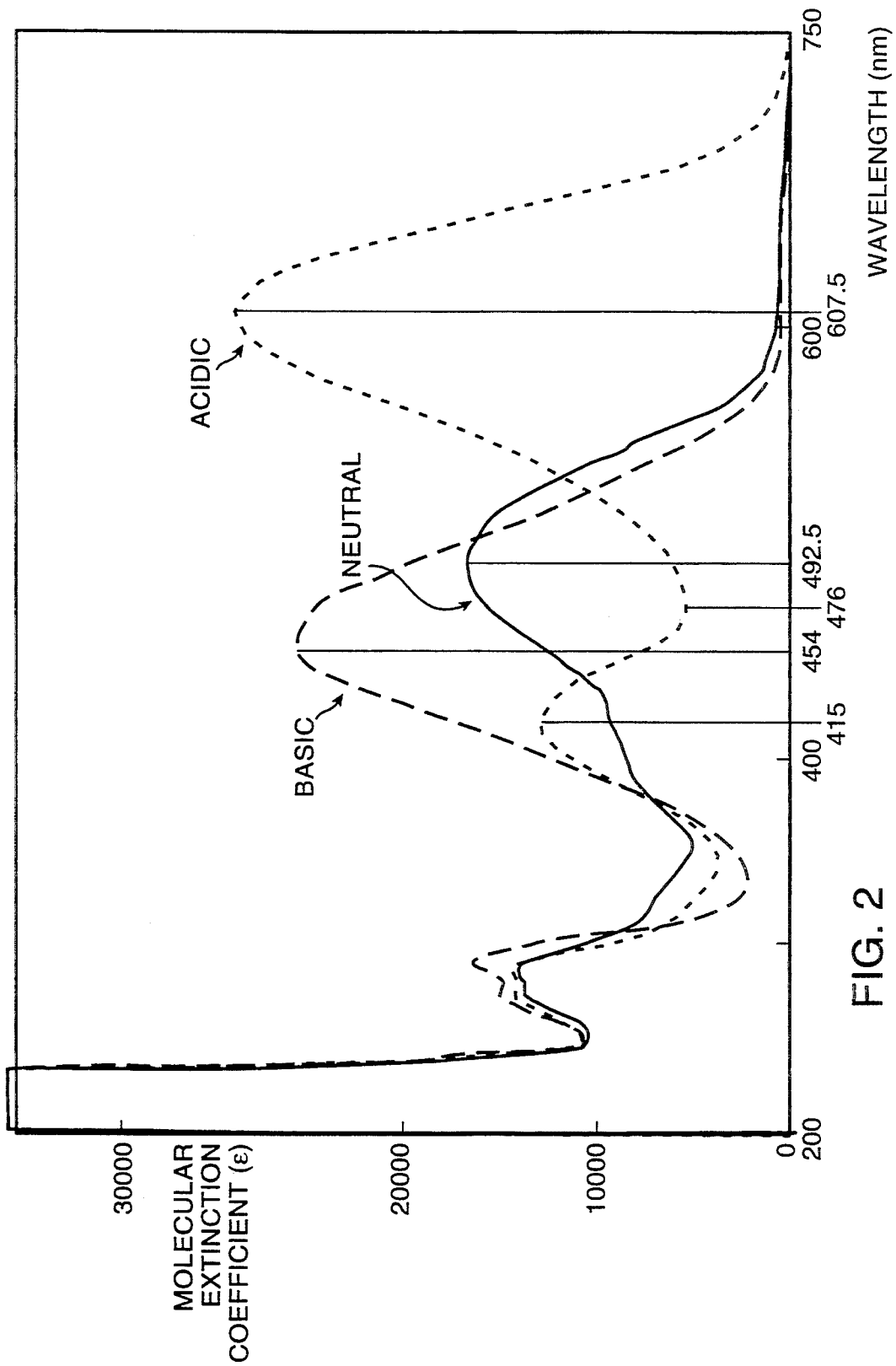
FIG. 2 is a UV spectrum of HS-1.

(5) UV Spectrum
Shown in FIG. 2.

| | | |
|---|---|---|
| λMeOHMAX | ($\epsilon$) nm | 492.5 (15624) |
| λMeOH—HClMAX | ($\epsilon$) nm | 415 (11904) |
| | | 607.5 (26705) |
| λMeOH—NaOH MAX | ($\epsilon$) nm | 454 (23809) |

Figure 3:
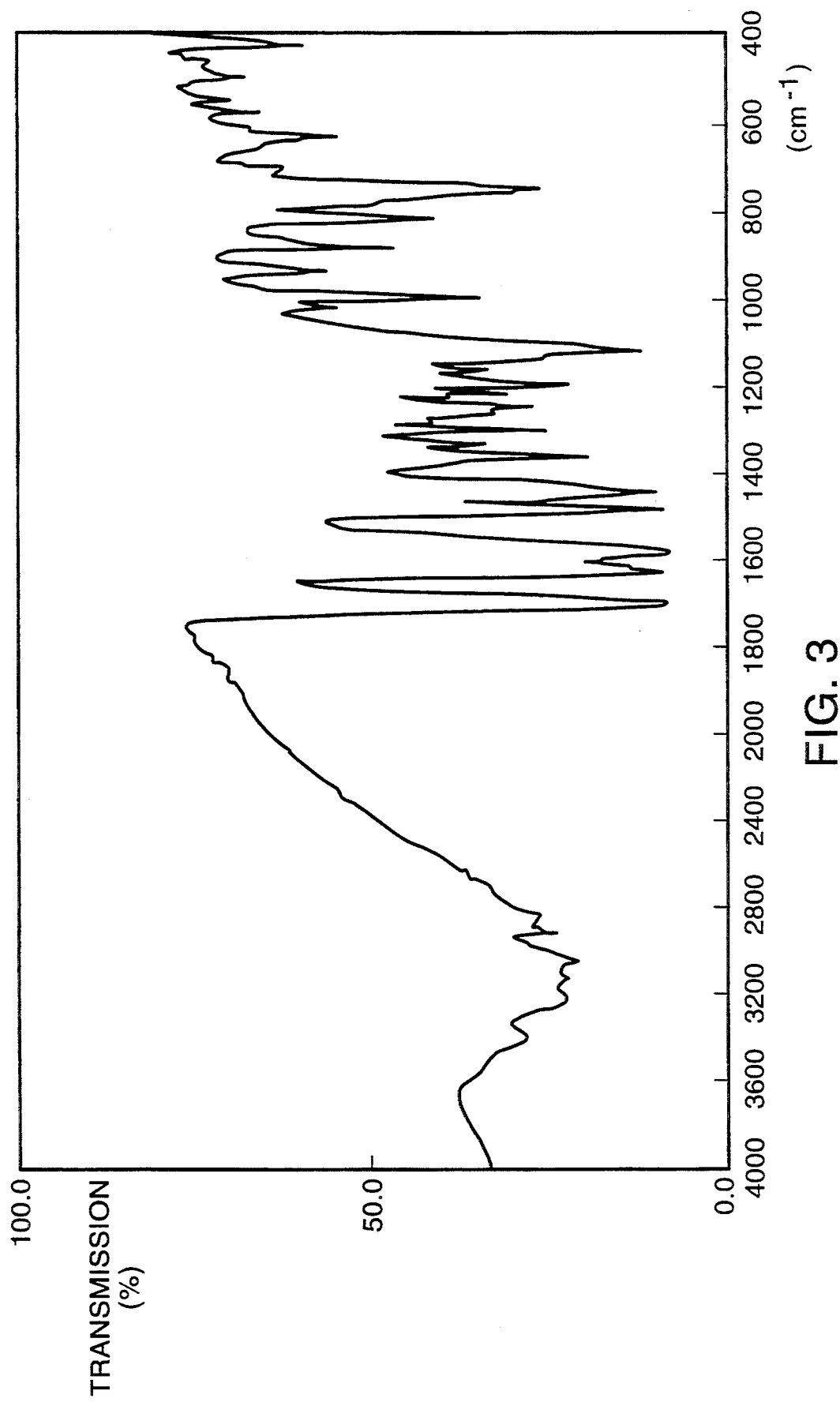
FIG. 3 is an IR spectrum of HS-1.

(6) IR Spectrum (KBr)
Shown in FIG. 3.

(7) $^1$H NMR Spectrum (200 MHz)
Measured using TMS as a standard in dimethyl sulfoxide-$d_6$ under basic conditions (NH$_3$ saturation).
6.91, 7.05, 7.14, 7.19, 7.37, 7.44, 7.45, 7.57, 7.75, 8.30, 8.76, 11.08 (ppm)

Figure 4:
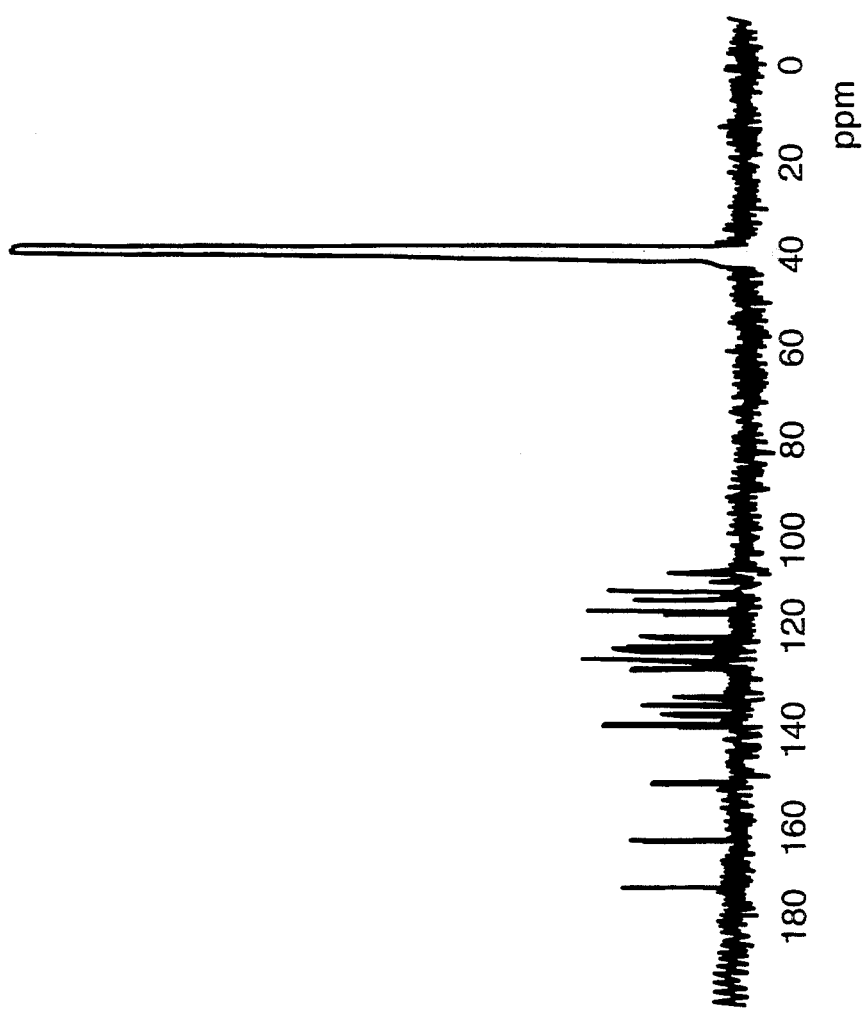
FIG. 4 is a 13C NMR (50 MHz) spectrum of HS-1.

(8) $^{13}$C NMR Spectrum (50 MHz)
Measured using TMS as a standard in dimethyl sulfoxide-$d_6$ under acidic conditions (with the addition of HCl). The results are shown in FIG. 4.

(9) Solubility
Readily soluble in dimethyl sulfoxide, scarcely soluble in methanol, and insoluble in water.

(10) Color and property
Dark red powder

(11) Thin layer chromatography
Rf values shown in Table 1 were determined by the TLC analysis using a silica gel plate (Art 5719, a product of Merck Co.) as a carrier.

TABLE 1

| Development solvent | Rf |
|---|---|
| Chloroform/methanol (95:5) | 0.08 |
| Chloroform/methanol (5:1) | 0.68 |

(12) HPLC Analysis
The retention time of this compound HS-1 was measured at 220 nm using a 45:55 mixed solvent of acetonitrile and 0.01% HCOOH aqueous solution and a reverse phase column (Sensyu Pak ODS-1251-N, 4.6×250 mm, manufactured by Senshu Science Co.) at a flow rate of 1 ml/min, and was found to be 15.4 minutes.

Based on the above analysis, the physiologically active compound of HS-1 of the present invention was confirmed to have the chemical structure shown in formula (I).

This compound forms pharmaceutically acceptable salts with hydrochloric acid, acetic acid, oxalic acid, lactic acid, citric acid, fumaric acid, maleic acid, or the like. These salts are included in the present invention.

The physiologically active compound HS-1 of the present invention have the following physiological characteristics.

<Physiological Characteristics>

(1) Antitumor activity
Human epidermoid carcinoma (oral) cell KB was inoculated into 96-well microplates (4000 cells/200 μl/well) and cultured in DMEM medium (containing 5% FCS) in 5% CO$_2$ at 37° C. for 24 hours. 5 μl of HS-1 solutions in DMSO at various HS-1 concentrations were added to above culture. After the culture incubated for 72 hours, 10 μl of a 2.5 mg/ml MTT solution was added and incubator was continued for a further 4 hours, thus producing formazan. After the addition of 200 μl of DMSO, the absorption at 540 nm was measured using an imunoreader. The cytocidal activity of HS-1 for KB cells was determined from the ratio of the absorption of the compound to the absorption of the control. The results are shown in Table 2.

TABLE 2

| Antitumor activity | |
|---|---|
| Name of cell | TC$_{50}$ (μg/ml) |
| KB | 0.68 |

(2) Antimicrobial activity
Antimicrobial activity of HS-1 was examined using eleven kinds of bacteria, fungi, and yeasts using paper discs with a diameter of 8 mm, at a concentration of 40 μg/disc. The results are shown in Table 3, wherein the antimicrobial activity of HS-1 is indicated as the diameter of the inhibition zone.

TABLE 3

| Antimicrobial activity of HS-1 | |
|---|---|
| Microorganism | Inhibition zone (mm) |
| *Escherichia coli* AB 1157 | 0 |
| *Escherichia coli* BE 1196 | 0 |
| *Pseudomonas aeruginosa* N-10 (L-form) | + |
| *Staphylococcus aureus* IFO 12732 | 0 |
| *Bacillus subtilis* rec + | 0 |
| *Bacillus subtilis* rec − | + |
| *Mycobacterium phlei* IFO 11158 | 0 |
| *Xanthomonas oryzae* IFO 331.2 | 11.9 |
| *Xanthomonas citri* IFO 3781 | 0 |
| *Botrytis cinerea* IFO 5365 | 0 |
| *Schizosaccharomyces pombe* IFO 0638 | 0 |

+: indicates an inhibition zone of 10 mm or smaller.
rec +: Wild strain
rec −: Repair activity defective strain The physiologically active compound HS-1 of the present invention is considered to be produced in the course of biosynthesis of violacein. The toxicity of HS-1 is expected to be as extremely low as violacein.

This compound can be produced by culturing Chromobacterium violaceum and collected from the culture broth or the culture cells. In the practice of the present invention, although HS-1 can be prepared using Chromobacterium violaceum ATCC 12472 (or JCM 1249) as disclosed in the examples hereinafter, it is possible to prepare it using other Chromobacterium violaceum microorganisms which are known to produce violacein. The Chromobacterium violaceum ATCC 12472 can be available from The American Type Culture Collection (ATCC).

Chromobacterium violaceum can be cultured in any nutritious culture media which are used for the culture of common microorganisms. Nutritional sources for this microorganism which can be utilized as nitrogen sources such as commercially available peptone, meat extract, corn steep liquor, cotton oil, soybean oil, yeast extract, NZ-amine, casein hydrolyzate, sodium nitrate, ammonium nitrate, and ammonium sulfate; carbon sources which are carbohydrates and the like, such as glycerine, sucrose, starch, glucose, mannose, galactose, and molasses. Furthermore, inorganic salts, such as sodium chloride, phosphates, calcium carbonate, magnesium sulfate, may be added to the culture. For the mass production of HS-1, liquid culture is preferred for culturing Chromobacterium violaceum. The temperature of the range in which the microorganism can grow can be employed for the production, although such a temperature range may vary depending on the cell lines selected. After sufficient growth of the cells, tryptophan and diethyldithio-carbamate (DDC) are added to the medium to the concentrations of 1–50 g/l and 10–100 g/l, respectively. The culture is continued for the production of physiologically active compound HS-1 by the cells. Alternatively, the grown cells may be harvested and charged in a buffer containing tryptophan and diethyldithiocarbamate (DDC) at concentrations of 1–50 g/l and 10–100 g/l, respectively, following which the solution is gently stirred at 20°–30° C. for the cells to produce the physiologically active compound HS-1. The physiologically active compound HS-1 is normally produced in the cells. However, it is possible to disrupt the cells by a ultrasonic treatment or the like, and to add the disrupted cells to a buffer containing tryptophan at a concentration of 1–50 g/l, followed by gentle stirring at 20°–30° C. for the production of the physiologically active compound HS-1.

After the addition of tryptophan and DDC and further culture for the production of the physiologically active compound HS-1, the cells are collected and HS-1 is extracted from the cells. In this case, the cells may be disrupted directly or by a ultrasonic treatment or the like, following which HS-1 is extracted with a solvent. Any polar solvents may be used for the extraction, with an especially preferred solvent being methanol. The extract is then subjected to a suitable combination of typical purification and isolation means such as chromatography, gel permeation chromatography, and HPLC, in order to obtain pure physiologically active compound HS-1 of the present invention.

The purified physiologically active compound HS-1 is prepared into tablets, powders, capsules, injection preparations, inhalation preparations, or preparations for external application. They are clinically applied by oral or non-oral administration. A dose is suitably determined depending on the symptoms of the diseases to be treated and the manner of the administration.

Because the physiologically active compound HS-1 provided by the present invention exhibits toxicity against cancer cells, it can be used as a novel type anti-tumor agent. Furthermore, due to its antimicrobial activity, this compound can be used as an antimicrobial agent.

Other features of the invention will become apparent in the course of the following description of the exemplary embodiments which are given for illustration of the invention and are not intended to be limiting thereof.

EXAMPLES

Example 1

Chromobacterium violaceum ATCC 12472 cultured in a slant agar medium, was cultured in a nutrient broth (a medium prepared by dissolving 3 g of meat extract, 5 g of polypeptone, and 5 g of NaCl in 1 l of water and adjusted to pH 7) containing 0.1% Tween #80 at 25° C. for 20 hours to provide a preculture liquid. 10 ml of this preculture liquid was charged to a 2 l Erlenmeyer flask containing 1 l of the same medium and cultured at 25° C. and 180 rpm for 12 hours. 87 l of the culture broth was centrifuged to collect the cells. The cells were washed with a physiological saline solution (0.85% NaCl) and suspended in 8.7 l of a 5.7 mM phosphate buffer (pH 7.0) in which 4.35 g of tryptophan and 24.0 g of DDC were dissolved, followed by shake culture at 25° C. and 200 rpm for 24 hours. The cells were collected by centrifuge and extracted several times with methanol. The extract was concentrated and added to hot water. The pigment was adsorbed by ion-exchange resin Amberlite XAD-2 (manufactured by Rhome and Haas Co.). The Amberlite XAD-2 was collected and washed with 10% methanol. The pigment adsorbed was then resolved by adding methanol to the Amberlite XAD-2 and heating the mixture. The pigment was collected, dissolved in a small amount of methanol, and submitted to Sephadex LH-20 (manufactured by Pharmacia) for elution with methanol. Orange color MS-1 fractions were collected and concentrated to obtain 42.2 mg of the physiologically active compound HS-1.

Example 2

Washed cells of Chromobacterium violaceum JCM1249, cultured in the same manner as in Example 1, were suspended in 4.35 l of 0.1M phosphate buffer (containing 10 mM 2-mercaptoethanol, 0.811 mM magnesium sulfate, and 2% triton X-100). The cells were ultrasonically disrupted while cooling below 8° C. with cold methanol. The disrupted cells were suspended in 500 ml of a 5.7 mM phosphate buffer (pH 7.0) in which 4.35 g of tryptophan was dissolved and shake cultured at 25° C. and 200 rpm for 24 hours. The cells were collected by centrifuge and extracted several times with methanol. The extract was concentrated, added to hot water. The pigment was adsorbed by ion-exchange resin Amberlite XAD-2. The Amberlite XAD-2 were collected and washed with 10% methanol. The pigment adsorbed was then resolved by adding methanol to the Amberlite XAD-2 and heating the mixture. The pigment was collected, dissolved in a small amount of methanol, and submitted to Sephadex LH-20 (manufactured by Pharmacia) for elution with methanol. Orange color HS-1 fractions were collected and concentrated to obtain 42.2 mg of the physiologically active compound HS-1.

TLC and HPLC analysis of this product exhibited a single spot and a single peak, respectively, confirming that it was pure physiologically active compound HS-1.

Obviously, numerous modifications and variations of the present invention are possible in light of the above teachings. It is therefore to be understood that within the scope of the appended claims, the invention may be practiced otherwise than as specifically described herein.

What is claimed is:

1. A physiologically active compound HS-1 represented by the following chemical formula (I),

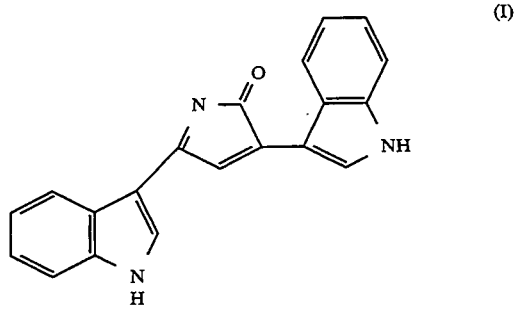
or a pharmaceutically acceptable salt thereof.
* * * * *